US008728465B2

(12) United States Patent
Black et al.

(10) Patent No.: US 8,728,465 B2
(45) Date of Patent: May 20, 2014

(54) USE OF TOLL-LIKE RECEPTOR LIGANDS AS ADJUVANTS TO VACCINATION THERAPY FOR BRAIN TUMORS

(75) Inventors: Keith L. Black, Los Angeles, CA (US); Dwain Morris-Irvin, Los Angeles, CA (US); Moshe Arditi, Encino, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 586 days.

(21) Appl. No.: 12/995,434

(22) PCT Filed: Jun. 17, 2009

(86) PCT No.: PCT/US2009/047640
§ 371 (c)(1),
(2), (4) Date: Nov. 30, 2010

(87) PCT Pub. No.: WO2009/155332
PCT Pub. Date: Dec. 23, 2009

(65) Prior Publication Data
US 2011/0104210 A1      May 5, 2011

Related U.S. Application Data

(60) Provisional application No. 61/073,205, filed on Jun. 17, 2008.

(51) Int. Cl.
| A01N 63/02 | (2006.01) |
| A61K 39/00 | (2006.01) |
| A61K 35/12 | (2006.01) |
| A61K 35/74 | (2006.01) |
| A61K 38/07 | (2006.01) |
| A61K 38/08 | (2006.01) |
| C07H 21/04 | (2006.01) |

(52) U.S. Cl.
USPC .............. 424/93.71; 424/277.1; 424/282.1; 424/283.1; 424/573; 424/780; 435/325; 435/374; 435/375; 530/327; 530/330; 536/25.6; 514/21.6; 514/21.9; 514/53; 514/54

(58) Field of Classification Search
None
See application file for complete search history.

(56) References Cited

U.S. PATENT DOCUMENTS

| 5,484,596 | A | 1/1996 | Hanna, Jr. et al. |
| 2001/0036458 | A1 | 11/2001 | Hiserodt et al. |
| 2003/0175247 | A1* | 9/2003 | Salgaller et al. ............. 424/93.7 |
| 2005/0136434 | A1 | 6/2005 | Xu |
| 2007/0280929 | A1 | 12/2007 | Hoerr et al. |
| 2008/0044441 | A1 | 2/2008 | Berd |
| 2008/0124366 | A1 | 5/2008 | Ohlfest et al. |
| 2008/0199485 | A1 | 8/2008 | Kundig et al. |
| 2011/0257458 | A1 | 10/2011 | Morris-Irvin et al. |

FOREIGN PATENT DOCUMENTS

| WO | WO 01/87325 | * 11/2001 |
| WO | WO 2009/155332 A1 | 12/2009 |
| WO | WO 2010/075525 A1 | 7/2010 |

OTHER PUBLICATIONS

Pilon-Thomas (Journal of Immunotherapy, 2006, vol. 29, pp. 381-387).*
Abstract of Prins et al (Journal of Clinical Oncology, May 20, 2008, supplement, Abstract No. 11021).*
Vicari et al (Journal of Experimental Medicine, 2002, vol. 196, pp. 541-549).*
Abstract of You et al (Zhonghua Yi Xue Za Zhi, Oct. 23, 2007, vol. 87, pp. 2785-2790).*
Yu et al (Cancer Research, 2004, vol. 64, pp. 4973-4979).*
Moneeb et al (Cancer Control, 2004, vol. 11, pp. 192-207).*
Figdor et al (Nature Medicine, 2004, vol. 10, pp. 475-480).*
Shubina et al (Experimental Immunology, 2007, vol. 32, pp. 189-195).*
The abstract of Semenov et al (Molekulyarnaya Meditsina, 2005, vol. 4, pp. 53-58).*
Schwandner et al (Journal of Biological Chemistry, 1999, vol. 274, pp. 17406-17409).*
Uehori et al (Infection and Immunity, 2003, vol. 71, pp. 4238-4249).*
Yamanaka et al (British Journal of Cancer, 2003, vol. 89, pp. 1172-1179).*
PCT/US2009/047640 Written Opinion dated Aug. 7, 2009.
PCT/US2009/047640 International Preliminary Report on Patentability dated Dec. 18, 2010.
PCT/US2009/069437 International Search Report dated Feb. 25, 2010.
PCT/US2009/069437 Written Opinion dated Feb. 25, 2010.
PCT/US2009/069437 International Preliminary Report on Patentability dated Jun. 29, 2011.
Chicoine et al. The in vivo antitumoral effects of lipopolysaccharide against glioblastoma multiforme are mediated in part by toll-like receptor 4. Neurosurgery (2007) 60(2):372-381.
De et al. Human glioma tumour-associated antigens. Cancer Immunol Immunother (1980) vol. 9(4):207-211. Abstract Only.
El Andaloussi et al. Stimulation of TLR9 with CpG ODN enhances apoptosis of glioma and prolongs the survival of mice with experimental brain tumors. GLIA (2006) 54:526-535.
Hussain et al. The role of human glioma-infiltrating microglia/macrophages in mediating antitumor immune responses. Neuro-Oncology (2006) pp. 261-279.
Hussain et al. Innate immune functions of microglia isolated from human glioma patients. Journal of Translational Medicine. (2006) 4(15): 9 pages.
Iizuka et al. Identification of a new antigen recognized by cytotoxic T lymphocytes specific for glioma. Society for Neuroscience Abstract Viewer and Itinerary Planner. (2003): Abstract Only.
Lichtor et al. Antigenic differences between normal and malignant cells as a basis for treatment of intracerebral neoplasms using a DNA-based vaccine. Current Genomics (2006) 7(4):253-261.
Mariani et al. Nonspecific immunotherapy with intratumoral lipopolysaccharide and zymosan A but not GM-CSF leads to an effective anti-tumor response in subcutaneous RG-2 gliomas. J. Neurooncol (2007) 85:231-240.

(Continued)

Primary Examiner — Karen Canella
(74) Attorney, Agent, or Firm — Linda B. Huber; Nixon Peabody LLP

(57) ABSTRACT

Compositions comprising dendritic cells pulsed with tumor lysate and at least one toll-like receptor (TLR) ligand which may be used for eliciting a specific immune response in a mammal in need thereof for treating diseases including a tumor are disclosed. Also disclose are methods of activating dendritic cells, comprising providing at least one toll-like receptor (TLR) ligand; and pulsing a dendentic cell with the at least one TLR ligand. A method further comprises pulsing the dendritic cell with a tumor lysate.

25 Claims, 8 Drawing Sheets

(56) References Cited

OTHER PUBLICATIONS

Prins et al. Cellular immunity and immunotherapy of brain tumors. Frontiers in Bioscience (2004) 9: 3124-3136.

Prasad et al. Recent advances in experimental molecular therapeutics for malignant gliomas. Curr Med Chem—Anti-Cancer Agents (2004) 4: 347-361.

Romodanov et al. Efficacy of experimental active specific immunotherapy and immunoprevention of malignant gliomas of the braina. Zh Vopr Neirokhir Im N N Burdenko (1986) Abstract Only Reizenstein et al. Biological Response to Acute Leukemia. I. Tumor-Associated Antigens and Antigen-Independent Tumor Surveillance. Cancer Treatment Symposia (1985). 1:101-105.

Scheel et al. Therapeutic anti-tumor immunity triggered by injections of immunostimulating single-stranded RNA. Eur. J. Immunol. (2006) 36:2807-2816.

Tracey et al. Growth of transplanted rat tumors following administration of cell-free tumor antigens. Cancer Research (1978). 38:1208-1212.

Ueda et al. Induction of protective and therapeutic antitumor immunity by a DNA vaccine with a glioma antigen, SOX6. Int. J. Cancer (2008). 122(10). Abstract Only.

Wu et al. In vivo vaccination with tumor cell lysate plus CpG oligodeoxynucleotides eradicates murine glioblastoma. J Immunother. (2007) 30(8):789-797.

Zhu et al. Toll Like Receptor-3 Ligand poly-ICLC promotes the efficacy of peripheral vaccinations with tumor antigen-derived peptide epitopes in murine CNS tumor models. Journal of Translational Medicine (2007) 5(10): 15 pages.

* cited by examiner

A.     B.

C

D

Vaccination and TLR Adjuvants : Survival Study

A.

B.

C.

D.

E.

F.

USE OF TOLL-LIKE RECEPTOR LIGANDS AS ADJUVANTS TO VACCINATION THERAPY FOR BRAIN TUMORS

CROSS-REFERENCE TO RELATED APPLICATIONS

This application is the National Phase of International Application PCT/US09/47640, filed Jun. 17, 2009, which designated the U.S. and that International Application was published under PCT Article 21(2) in English. This application also includes a claim of priority under 35 U.S.C. §119(e) to U.S. provisional patent application No. 61/073,205, filed Jun. 17, 2008.

FIELD OF INVENTION

This invention relates to the treatment of cancer using vaccination therapy.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Cancer remains among the leading causes of death in the United States and around the world. Various forms of cancer are differentially treated, depending in part on the location of a tumor. One particularly difficult group of tumors to treat includes those that reside in and near the brain. Treatment of brain tumors presents a number of problems, not the least of which being the dangers inherent in any surgical procedure involving regions of the brain and the tissue located nearby. There is little room for error and the consequences of even a minor surgical mishap can be devastating to a patient; brain damage, or even death may result. Still, where possible, surgery remains the preferred method of treatment for most brain tumors and is often performed in conjunction with radiation therapy and chemotherapy. However, even commonly referenced medical authority suggests that patients with brain tumors be referred to centers specializing in investigative therapies; an indication that conventional modes of treatment are not overwhelmingly successful.

Glioblastoma multiforme and anaplastic astrocytomas are classified in the category of brain tumors commonly known as malignant gliomas. Although not particularly common tumors themselves, they represent a class of tumors associated with significant rates of mortality and morbidity. Current treatment for malignant glioma consists of surgical resection followed by radiation therapy and chemotherapy. However, this treatment generally fails in substantially changing the outcome for a patient; median survival remains less than one year even with medical intervention.

Antitumor dendritic cell ("DC") vaccination strategy (e.g., using DCs pulsed with tumor lysate) shows encouraging results, but in most cases fails to completely eradicate the tumor. Thus, there exists a significant need in the art for the development dendritic cell based immunotherapy with improved efficacy in eradicating tumors.

SUMMARY OF THE INVENTION

The following embodiments and aspects thereof are described and illustrated in conjunction with compositions and methods which are meant to be exemplary and illustrative, not limiting in scope.

The present invention provides for compositions comprising: a dendritic cell pulsed with tumor lysate and at least one toll-like receptor (TLR) ligand. In one embodiment the compositions may further comprise a pharmaceutically acceptable carrier.

In various embodiments, the dendritic cell may be an autologous dendritic cell or an allogeneic dendritic cell.

In various embodiments, the at least one TLR ligand may be selected from the group consisting of a TLR2 ligand, TLR4 ligand, TLR9 ligand and combinations thereof. In certain embodiments, the at least one TLR ligand may be selected from the group consisting of Pam3cys, PolyI:C, lipopolysaccharide ("LPS"), ST-FLA, Gardiquimod, CpG ODN, TLR1/2 Agonist: Pam3CSK4, TLR2 Agonist: HKLM, TLR3 Agonist: Poly(I:C), TLR4 Agonist: LPS E. coli, TLR5 Agonist: Flagellin S. typhimurium, TLR6/2 Agonist: FSL1, TLR7 Agonist: Imiquimod, TLR8 Agonist: ssRNA40, TLR9 Agonist: ODN and combinations thereof. In a particular embodiment, the at least one TLR ligand is a combination of Pam3cys, LPS and CpG ODN.

In various embodiments, the tumor lysate may from a tumor selected from the group consisting of breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, and brain cancer. In certain embodiments, the brain cancer may be selected from the group consisting of glioma, glioblastoma, glioblastoma multiforme (GBM), oligodendroglioma, primitive neuroectodermal tumor, astrocytoma, ependymoma, oligodendroglioma, medulloblastoma, meningioma, pituitary carcinomas, neuroblastoma, and craniopharyngioma. In a particular embodiment, the tumor lysate may be from a glioma.

The present invention also provides for methods of eliciting a specific immune response in a mammal in need thereof, comprising: providing a composition comprising: a dendritic cell pulsed with tumor lysate and at least one toll-like receptor (TLR) ligand (as described above and in more detail below); and administering the composition to the mammal to elicit the specific immune response. In one embodiment, the composition may further comprise a pharmaceutically acceptable carrier.

The present invention also provides methods of activating dendritic cells, comprising: providing at least one toll-like receptor (TLR) ligand; and pulsing a dendritic cell with the at least one TLR ligand.

In various embodiments, the at least one TLR ligand may be selected from the group consisting of a TLR2 ligand, TLR4 ligand, TLR9 ligand and combinations thereof. In certain embodiments, the at least one TLR ligand may be selected from the group consisting of Pam3cys, PolyI:C, lipopolysaccharide ("LPS"), ST-FLA, Gardiquimod, CpG ODN, TLR1/2 Agonist: Pam3CSK4, TLR2 Agonist: HKLM, TLR3 Agonist: Poly(I:C), TLR4 Agonist: LPS E. coli, TLR5 Agonist: Flagellin S. typhimurium, TLR6/2 Agonist: FSL1, TLR7 Agonist: Imiquimod, TLR8 Agonist: ssRNA40, TLR9 Agonist: ODN and combinations thereof. In a particular embodiment, the at least one TLR ligand may be a combination of Pam3cys, LPS and CpG ODN.

In various embodiments, the dendritic cell may be an autologous dendritic cell or an allogeneic dendritic cell.

In a further embodiment, the method further comprises pulsing the dendritic cell with a tumor lysate.

In various embodiments, the tumor lysate may be from a tumor selected from the group consisting of breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, and brain cancer. In certain embodiments, the brain cancer may be selected from the group consisting of glioma, glioblastoma, glioblastoma multiforme (GBM), oligodendroglioma, primitive neuroectodermal tumor, astrocytoma, ependymoma, oligodendroglioma, medulloblastoma, meningioma, pituitary carcinomas, neuroblastoma, and craniopharyngioma. In a particular embodiment, the tumor lysate may be from a glioma.

The present invention also provides for kits for eliciting a specific immune response in a mammal in need thereof, comprising: a composition comprising: a dendritic cell pulsed with tumor lysate and at least one toll-like receptor (TLR) ligand (as described above and in more detail below); and instructions for administering the composition to the mammal to elicit the specific immune response. In one embodiment, the composition may further comprise a pharmaceutically acceptable carrier.

The present invention also provides for kits for activating dendritic cells, comprising: at least one toll-like receptor (TLR) ligand (as described above and in more detail below); and instructions for using the at least one TLR ligand to activate the dendritic cells.

Other features and advantages of the invention will become apparent from the following detailed description, taken in conjunction with the accompanying drawings, which illustrate, by way of example, various features of embodiments of the invention.

BRIEF DESCRIPTION OF THE FIGURES

Exemplary embodiments are illustrated in referenced figures. It is intended that the embodiments and figures disclosed herein are to be considered illustrative rather than restrictive.

DESCRIPTION OF THE INVENTION

Figure 1:
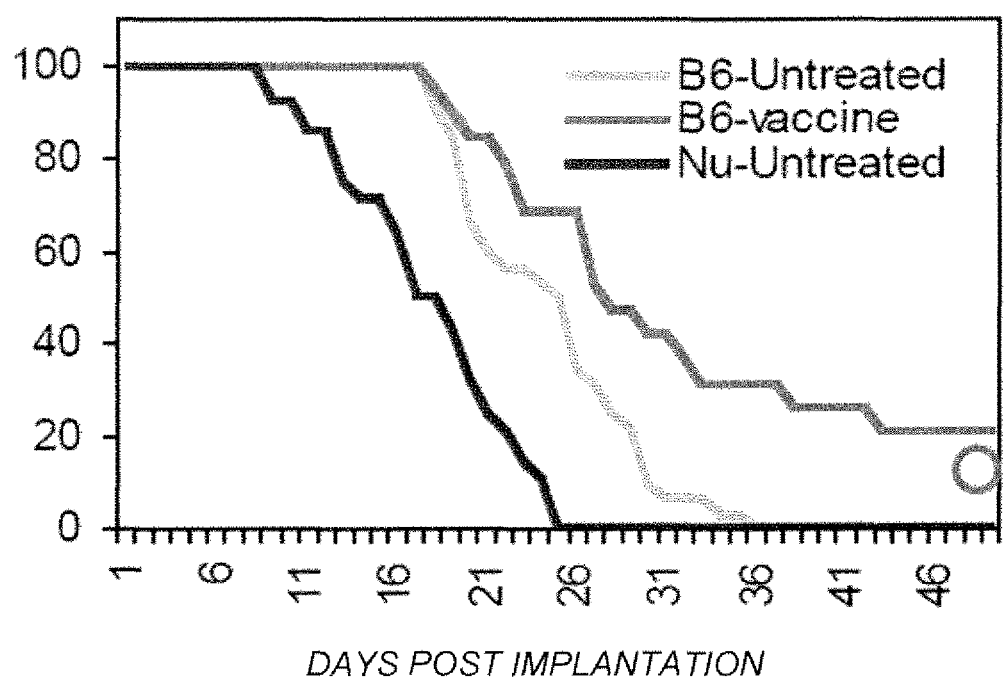
FIG. 1 shows that vaccination improves survival in GL26 glioma bearing mice in accordance with an embodiment of the present invention. Nude (n=28) and wild-type mice (n=32) received intracranial implants of 50,000 GL26 cells, but no vaccination treatment. Experimental wild-type mice (n=19) also received intracranial implants of 50,000 GL26 cells, but were vaccinated with $2 \times 10^6$ GL26 lysate-pulsed DC2.4 cells at 3 days and again at 7 days post-implantation. DC-vaccinated mice survived significantly longer relative to either untreated wild-type or untreated nude mice (P<0.003). Untreated immunocompetent wild-type mice survived significantly longer than untreated immunocompromised mice.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., J. Wiley & Sons (New York, N.Y. 2001); March, *Advanced Organic Chemistry Reactions, Mechanisms and Structure* 5$^{th}$ ed., J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

"Mammal" as used herein refers to any member of the class Mammalia, including, without limitation, humans and non-human primates such as chimpanzees, and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus adult and newborn subjects, as well as fetuses, whether male or female, are intended to be including within the scope of this term.

"Therapeutically effective amount" as used herein refers to that amount which is capable of achieving beneficial results in a patient with a tumor. A therapeutically effective amount can be determined on an individual basis and can be based, at least in part, on consideration of the physiological characteristics of the mammal, the type of delivery system or therapeutic technique used and the time of administration relative to the progression of the disease.

"Cancer" and "cancerous" refer to or describe the physiological condition in mammals that is typically characterized by unregulated cell growth. Examples of cancer include, but are not limited to, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, and brain cancer; including, but not limited to, gliomas, glioblastomas, glioblastoma multiforme (GBM), oligodendrogliomas, primitive neuroectodermal tumors, low, mid and high grade astrocytomas, ependymomas (e.g., myxopapillary ependymoma papillary ependymoma, subependymoma, anaplastic ependymoma), oligodendrogliomas, medulloblastomas, meningiomas, pituitary carcinomas, neuroblastomas, and craniopharyngiomas.

"Pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

"Treatment" and "treating," as used herein refer to both therapeutic treatment and prophylactic or preventative measures, wherein the object is to prevent or slow down (lessen) the targeted pathologic condition or disorder even if the treatment is ultimately unsuccessful. Those in need of treatment include those already with the disorder as well as those prone to have the disorder or those in whom the disorder is to be prevented. For example, in tumor (e.g., cancer) treatment, a therapeutic agent may directly decrease the pathology of tumor cells, or render the tumor cells more susceptible to treatment by other therapeutic agents or by the subject's own immune system.

"Tumor," as used herein refers to all neoplastic cell growth and proliferation, whether malignant or benign, and all pre-cancerous and cancerous cells and tissues.

Antitumor DC vaccination strategy (with tumor lysate alone) shows encouraging results, but in most cases fails to completely eradicate the tumor. The inventors believe that the reason may be insufficient adjuvant stimulation of bone marrow derived dendritic cells ("BMDCs"), and the result is that the level of co-stimulatory molecule expression and pro-inflammatory cytokine expression by BMDCs is insufficient to mount an anti-tumor cytotoxic response that would eradicate the tumor. As described herein, the inventors improve the effectiveness of the BMDC vaccination strategy by treating primary BMDCs ex vivo with TLR adjuvants prior to adoptive transfer. The inventors believe that activation of BMDC with TLR2, 4 and 9 ligands increases the productivity of pro-inflammatory cytokines, co-stimulatory molecules and inhibitory molecules as compared to GL26 cell lysate alone.

Embodiments of the present invention are based, in part, on the inventors discovery that toll-like receptor ("TLR") ligands can be effectively utilized as adjuvants to vaccination therapy for the treatment of brain tumors; particularly, for gliomas. The treatment involves utilizing activators of the TLR signaling system as adjuvants to dendritic based vaccination against gliomas. The inventors' studies show that activation of dendritic cells with tumor lysate and TLR ligands improves the efficacy of dendritic cell based immunotherapy against gliomas. The studies provide evidence that there is significant improvement in survival in the animal model for gliomas.

One embodiment of the present invention provides for a composition for eliciting a specific immune response in a mammal in need thereof. Particularly, the composition can be a vaccine useful for treating a brain tumor in a mammal in need thereof. The composition comprises dendritic cells pulsed with tumor lysate and at least one TLR ligand.

The dendritic cells of the present invention may be autologous dendritic cells or allogeneic dendritic cells. Dendritic cells suitable for use in accordance with the present invention may be isolated or obtained from any tissue in which such cells are found, or may be otherwise cultured and provided. Dendritic cells may be found, for example, but in no way limited to, in the bone marrow, in peripheral blood mononuclear cells (PBMCs) of a mammal or in the spleen of a mammal. Additionally, any suitable media that promote the growth of dendritic cells may be used in accordance with the present invention, and may be readily ascertained by one skilled in the art.

In one particular embodiment, the tumor lysate may be lysate from a brain tumor, including but not limited to a glioma, glioblastoma, glioblastoma multiforme (GBM), oligodendroglioma, primitive neuroectodermal tumor, low, mid and high grade astrocytoma, ependymoma myxopapillary ependymoma papillary ependymoma, subependymoma, anaplastic ependymoma), oligodendroglioma, medulloblastoma, meningioma, pituitary adenoma, pituitary carcinoma, neuroblastoma, and craniopharyngioma.

In another particular embodiment, the TLR ligand may be selected from the group consisting of Pam3cys, PolyI:C, lipopolysaccharide ("LPS"), ST-FLA, Gardiquimod, CpG ODN, TLR1/2 Agonist: Pam3CSK4, TLR2 Agonist: HKLM, TLR3 Agonist: Poly(I:C), TLR4 Agonist: LPS *E. coli*, TLR5 Agonist: Flagellin *S. typhimurium*, TLR6/2 Agonist: FSL1, TLR7 Agonist: Imiquimod, TLR8 Agonist: ssRNA40, and TLR9 Agonist: ODN and combinations thereof. Particularly useful is dendritic cells pulsed with tumor lysate and a TLR ligand cocktail comprising the TLR ligands Pam3cys, LPS and CpG ODN.

Another embodiment of the present invention is a method of eliciting a specific immune response in a mammal in need thereof. The method comprises providing a composition comprising dendritic cells pulsed with tumor lysate and at least one TLR ligand as described above and administering the composition to a mammal. In a further embodiment, the method comprises administering an additional dose of the composition to the mammal.

In one embodiment, the method of eliciting a specific immune response is a method of treating a brain tumor. The method comprises providing a composition comprising dendritic cells pulsed with tumor lysate and at least one TLR ligand as described above and administering the composition to a mammal to treat the brain tumor. Brain tumors treated by the inventive method include but are not limited to gliomas, glioblastomas, glioblastoma multiforme (GBM), oligodendrogliomas, primitive neuroectodermal tumors, low, mid and high grade astrocytomas, ependymomas (e.g., myxopapillary ependymoma papillary ependymoma, subependymoma, anaplastic ependymoma), oligodendrogliomas, medulloblastomas, meningiomas, pituitary adenomas, pituitary carcinomas, neuroblastomas, and craniopharyngiomas.

The composition may be administered one or more times to the mammal to impart beneficial results. The composition may be administered prior or post surgical resection of a tumor. One skilled in the art will be able to determine the appropriate timing for administering the composition. The timing of the first and/or subsequent dose(s) of the composition may depend on a variety of factors, including, but not limited to a patient's health, stability, age, and weight. The composition may be administered at any appropriate time interval; for example, including but not limited to once per week, once every two weeks, once every three weeks, and once per month. In one embodiment, the composition may be administered indefinitely. In another embodiment, the composition may be administered three times in two week intervals. Appropriate dosage of the composition may also depend on a variety of factors, including, but not limited to a patient's health, stability, age, and weight. In one embodiment, the composition may comprise from about $10^4$ to about $10^9$ dendritic cells pulsed with tumor lysate and at least one TLR ligand as described above. In another embodiment, the composition may comprise from about $10^5$ to about $10^7$ dendritic cells pulsed with tumor lysate and at least one TLR ligand as described above. In another embodiment, the composition may comprise about $10^6$ to about $10^7$ dendritic cells pulsed with tumor lysate and at least one TLR ligand as described above.

Administering the composition may be performed in conjunction with other therapeutic treatments; for example, chemotherapy and radiation. In one embodiment, the inventive composition is administered by injection (i.e., intravenous, intraarterial, etc.). In another embodiment, the inventive composition may be administered directly into or in close proximity of the tumor. In another embodiment, the inventive composition may be administered directly into or in close proximity of the site of the resected tumor.

Another embodiment of the present invention provides for a method of producing the composition/vaccine of the present invention and a method of activating the dendritic cells. The method comprises providing dendritic cells; culturing the dendritic cells; pulsing the dendritic cells with tumor lysate and at least one TLR ligand (e.g., exposing the dendritic cells to tumor lysate and at least one TLR ligand, culturing the dendritic cells in the presence of tumor lysate and at least one TLR ligand). In various embodiments, the dendritic cells may be pulsed with tumor lysate at a concentration of about 50-1000 ug/$10^6$-$10^7$ PBMDCs, which can be effective at activating PBMDCs in vitro. The dendritic cells may be ones as described above. In a particular embodiment, the dendritic cells may be bone-marrow derived dendritic cells. The TLR ligand may be selected from the group consisting of Pam3cys, PolyI:C, lipopolysaccharide ("LPS"), ST-FLA, Gardiquimod, CpG ODN, TLR1/2 Agonist: Pam3CSK4, TLR2 Agonist: HKLM, TLR3 Agonist: Poly(I:C), TLR4 Agonist: LPS *E. coli*, TLR5 Agonist: Flagellin *S. typhimurium*, TLR6/2 Agonist: FLS1, TLR7 Agonist: Imiquimod, TLR8 Agonist: ssRNA40, and TLR9 Agonist: ODN and combinations thereof. It is also particularly useful to expose the dendritic cells to tumor lysate and a TLR ligand cocktail comprising the TLR ligands Pam3cys, LPS and CpG ODN.

In various embodiments, the present invention provides pharmaceutical compositions including a pharmaceutically acceptable excipient along with a therapeutically effective amount of the composition comprising dendritic cells pulsed with tumor lysate and at least one TLR ligand as described above. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

In various embodiments, the pharmaceutical compositions according to the invention may be formulated for delivery via any route of administration. "Route of administration" may refer to any administration pathway known in the art, including but not limited to aerosol, nasal, oral, transmucosal, transdermal or parenteral. "Parenteral" refers to a route of administration that is generally associated with injection, including intraorbital, infusion, intraarterial, intracapsular, intracardiac, intracarotid, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical preparations may be made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see *Remington: The Science and Practice of Pharmacy* (Gennaro ed. 20th edition, Williams & Wilkins PA, USA) (2000).

Typical dosages of an effective amount of the composition comprising dendritic cells pulsed with tumor lysate and at least one TLR ligand as described above can also be as indicated to the skilled artisan by the in vitro responses or responses in animal models. The actual dosage will depend upon the judgment of the physician, the condition of the patient, and the effectiveness of the therapeutic method based, for example, on the in vitro responsiveness of the relevant primary cultured cells or histocultured tissue sample, such as biopsied malignant tumors, or the responses observed in the appropriate animal models, as previously described.

The present invention is also directed to a kit to elicit a specific immune response in a mammal with a tumor or to treat a tumor; for example a brain tumor. The kit is useful for practicing the inventive method of eliciting an immune response in a mammal with a tumor or treating a tumor. The kit is an assemblage of materials or components, including at least one of the inventive compositions. Thus, in some embodiments the kit contains a composition comprising dendritic cells pulsed with tumor lysate and at least one TLR ligand as described above.

The exact nature of the components configured in the inventive kit depends on its intended purpose. In one embodiment, the kit is configured particularly for the purpose of treating mammalian subjects. In a particular embodiment, the kit is configured particularly for the purpose of treating human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to elicit a specific immune response in a mammal with a brain tumor or to treat a brain tumor, or to prepare the dendritic cells for injection into the mammal. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well known methods, preferably to provide a sterile, contaminant-free environment. The packaging materials employed in the kit are those customarily utilized in vaccination therapy. As used herein, the term "package" refers to a suitable solid matrix or material such as glass, plastic, paper, foil, and the like, capable of holding the individual kit components. Thus, for example, a package can be a glass vial used to contain suitable quantities of an inventive composition comprising dendritic cells pulsed with tumor lysate and at least one TLR ligand as described above. The packaging material generally has an external label which indicates the contents and/or purpose of the kit and/or its components.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

GL26 and DC2.4 Cell Lines are Well-Suited to Model Glioma and Vaccination Therapy in a Syngeneic Host In order to model glioma and test therapeutic vaccination approaches against glioma in rodents, the inventors utilize the GL26 cell line derived from C57BL/6 mice. In vivo studies utilize this model, which involves intracranial implantation into recipient mice. Other rodent models of implanted glioma are available and have been utilized in the inventors' laboratory over the years, however the inventors specifically selected this model because it allows incorporation of studies involving TRL2-, TLR4-, TLR9-, MyD88- and TRW-knockout mice. All these knockouts are bred against the C57BL/6 background. In mice, the inventors have performed intracranial implantation into the syngeneic host (wild-type C57BL/6), and the immunocompromised model, C57BL/6 Nu/Nu mice. Since the inventors' studies investigate immune mechanisms in GBM, use of an immunocompromised model such as the Nu/Nu mice is unsuitable. Data shown herein provides an additional reason why the Nu/Nu is not a good model as well; specifically, the mice succumb to tumor implantation significantly faster than immunocompetent mice. (see FIG. 1).

The inventors performed their previously described vaccination therapy against the GL26 tumor by ex vivo activation of the DC2.4 dendritic cell line with lysate obtained from GL26 cells. Subsequently, the inventors adoptively transferred $2 \times 10^6$ activated DC2.4 cells into the wild-type C57BL/6 mice (n=19) at day 3 and again at 7 days after intracranial implantation of 50,000 GL26 cells. Controls received no DC2.4 cells, but underwent intracranial implantation of 50,000 GL26 cells, and included athymic nude mice (n=28) and wild-type C57BL/6 mice (n=32). Survival was plotted after implantation, and compared with survival in untreated wild-type C57BL/6 mice that received GL26 implantation, but no DC-based vaccination therapy (Morris-Irvin et al: unpublished data). Immunocompromised (athymic Nu/Nu) mice that received GL26 implants had the shortest survival time, followed by untreated immunocompetent mice (wild-type C57BL/6). This finding is consistent with the inventors' general model, which proposes that a functional immune system is required to eradicate or at least slow the growth of GL26 glioma cells. All mice received implantation consisting of 50,000 GL26 cells.

As shown in the survival curves (FIG. 1), DC-vaccinated hosts survived significantly longer relative to either untreated wild-type mice or nude mice implanted simultaneously with 50,000 original GL26 tumor cells. Immunocompromised nude mice that received no DC vaccination treatment exhibited the shortest survival (median=17 days; range, 9-25 days), followed by wild-type immunocompetent mice that received no DC vaccination (median=27 days; range, 19-36 days) ($p<0.01$). Vaccinated wild-type mice survived significantly longer than unvaccinated wild-type mice (median=31 days) ($p<0.01$). Of the vaccinated mice, 20% of the animals survived until the end of the experiment (50 days). These data indicate that the effectiveness of vaccination therapy is strongly influenced by the presence or absence of a fully functional immune system, and thus supports the inventors' general model. However, only a small proportion (roughly 20%) of vaccinated mice survived until the end of the experiment. While not wishing to be bound by any particular theory, the believe that survival is significantly improved by adjuvant treatment of DCs ex vivo prior to adoptive transfer using TLR ligands.

However, it is possible that despite better survival in vaccine-treated mice, tumor killing was not enhanced, and so tumor size was not significantly different than in untreated tumor-bearing mice. For example, it could be that mice that received vaccination benefited from a nonspecific activation of host defenses that somehow prolonged survival, for example, by rendering the mice better able to fight infections. Alternatively, it is possible that survival was enhanced in vaccine-treated mice for some other nonspecific reason that was unrelated to immune-mediated tumor cytotoxicity. If survival is a surrogate for tumor size, then one would predict a highly significant inverse correlation between tumor size and survival that is independent of treatment condition. Another possible problem is that ex viva treatment of DCs with tumor lysate causes a nonspecific activation of host defenses that may or may not have secondarily improved tumor killing, or at least inhibited tumor growth. Nevertheless, the inventors' results described herein provide support that is at least consistent with the inventors' belief that activation of host defenses improves immune-mediated killing of tumor cells.

Example 2

Noninvasive Measurement of Tumor Size Using Luciferase-Expression GL26 Cells

Figure 2:
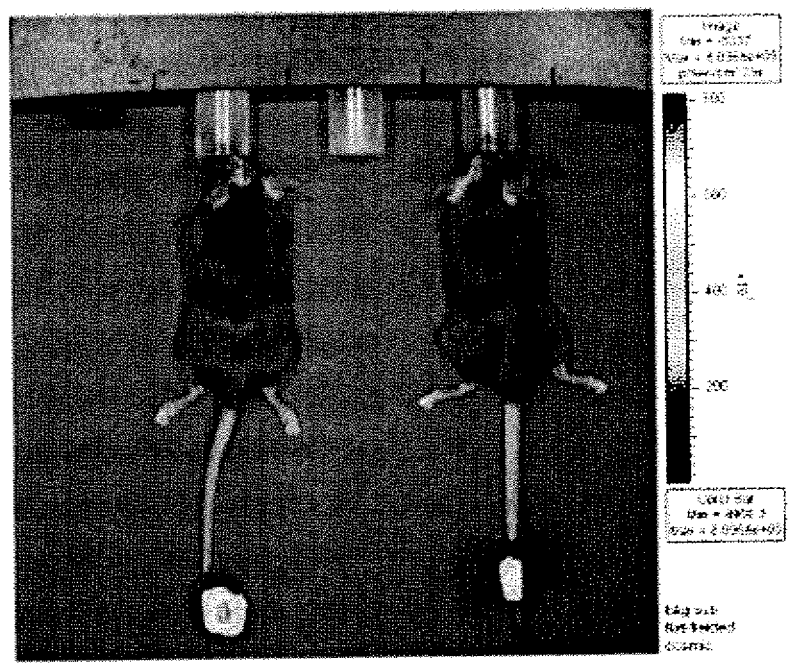
FIG. 2 shows that GL26 luciferase-expressing cells can be visualized using the Xenogen Living Imaging System in accordance with an embodiment of the present invention. (A-D) 100,000 GL26 luciferase-expressing cells were implanted into the striatum and 7 days later visualized after tail vein injection of luciferin substrate. Vaccination only (C); Vaccination with TLR cocktail (D).
Figure 2:
Figure 2:
Figure 3:
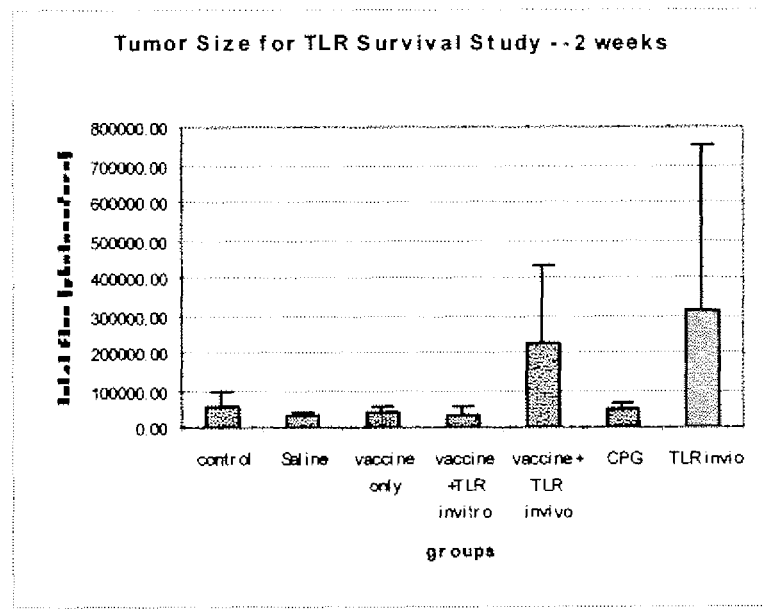
FIG. 3 depicts relative tumor volume from Xenogen luciferase in vivo imaging in accordance with an embodiment of the present invention.
Figure 4:
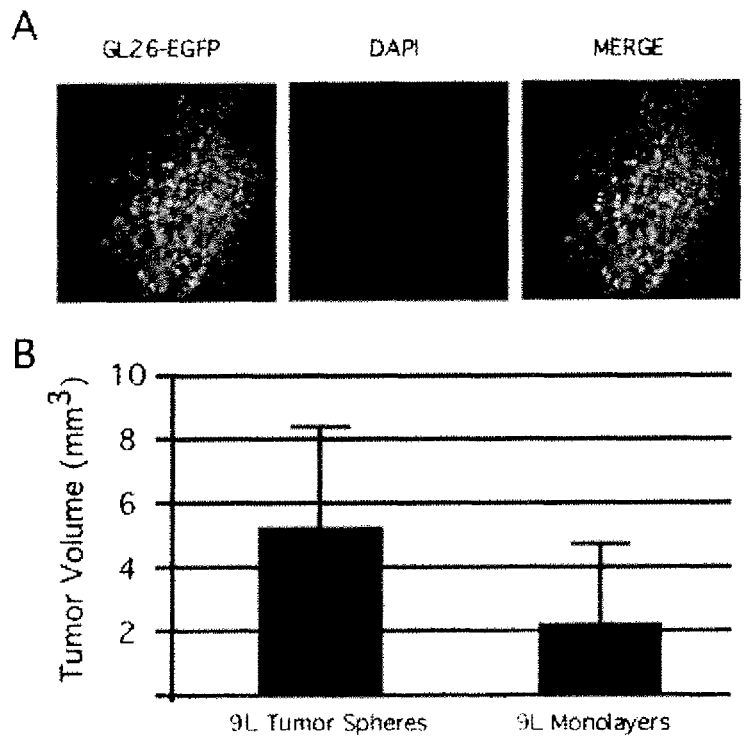
FIG. 4A shows that GL26 expressing cells can be used to identify and delineate the borders of a tumor in accordance with an embodiment of the present invention. The 9 L tumor cell line was utilized to generate a syngeneic rat model of glioma.
FIG. 4B depicts tumor volume in accordance with an embodiment of the present invention. The tumor volume is quantified by identifying the beginning and end of a tumor, then applying the equation for an ellipsoid to assess volume in a symmetrical tumor generated through the use of either the GL26 tumor line in C57B/6J mice or the 9 L tumor line in Fisher rats.

In order to follow the progression of tumors in vivo without having to euthanize the animal, the inventors sought a method for measuring tumor size that is suitable for in vivo serial imaging of tumors noninvasively. Therefore, the inventors utilized GL26 luciferase-expressing cells and utilized the Xenogen Living Imaging System to visualize light produced by the action of luciferin in vivo (Zu et al., *Molecular Cancer*, 2007). This method of visualizing the amount of light emitted as a representation of the overall volume of the tumor is quite valuable, in that the relative size of GL26 tumors over time in the same animal can be measured. FIG. 2 shows two wild-type (C57BL/6) mice that received a total of 100,000 GL26 cells implanted into the striatum. The inventors have chosen to use these cells in the model, as these cells will still allow one to examine the size of tumors over defined time periods as described herein. Tumor size can be evaluated noninvasively using the Xenogen bioluminescence imaging system and can also be quantified histopathologically using computer-assisted software. (FIGS. 3 and 4B.)

Example 3

An Alternative Method of Measuring Tumor Size: Use of GL26 Cells Expressing EGFP As an alternative for measuring tumor size, the inventors have generated GL26 cells that express EGFP by transducing GL26 cells with a retrovirus that encodes EGFP. After implantation, these cells express GFP and can delineate the borders of the tumor (FIG. 4A). It is essential that tumor mass and/or volume be accurately and reproducibly measured. Such measurements were performed histopathologically. For example, hematoxylin & eosin (H&E) histocytochemical staining was performed to identify the 9 L tumor cell line implanted into Fisher rats. Through the use of H&E, the borders of tumors were delineated. Subsequently, tumor volume was assessed by using the formula for an ellipsoid, (length×width×height)/2, with the height and the width of the tumor being approximately equal because of the well defined circumference of the tumors generated by the 9 L gliosarcoma, a feature that is also shared by the C57B/6J GL26 glioma model (Morris-Irvin et al.: unpublished). This method allows utilization of brain sections generated at a known thickness (e.g., 20 µm) derived from the animal models of glioma, and identifies the first section by which the tumor is identified and all subsequent sections are counted thereafter until the end of the tumor. The number of sections multiplied by the thickness of each section can be calculated and substituted into the equation for an ellipsoid to determine tumor volume (FIG. 4B). Use of GL26 cells that have been stably transfected with lentiviral constructs encoding GFP in implantation experiments could be problematic. There is no guarantee these cells will perform the same as non-transfected cells. Transfection with lentiviral constructs could itself influence the host immune response, for example, and make results of experiments proposed difficult to interpret. Therefore, validating the use of these cells in the model was performed to that ensure survival and all other dependent variables measured are analyzed and compared.

Example 4

Figure 5:
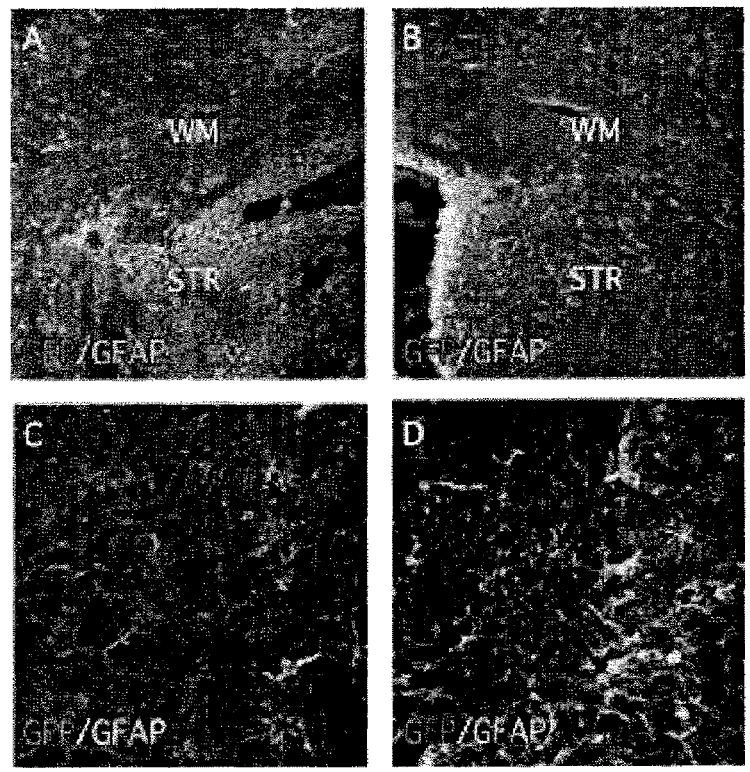
FIG. 5 depicts transgenic CD11cDTR-GFP mice utilized for GL26 tumor-cell intrastriatal implantation and sacrificed 2 weeks post-implantation in accordance with an embodiment of the present invention. Dendritic cells (GFP) and INC against GFAP (green) for astrocytes shows dendritic cell and astrocyte infiltration within the tumor-10X (A) compared to the contralateral control striatum-10X (B); Tumor-20X (C); Saline-20X (D). White matter ("WM"); striatum ("STR").

Activation of DC2.4 Dendritic Cells with Tumor Lysate and TLR Ligands Promote Survival in Glioma Mice DCs Infiltrate and/or Accumulate in Implanted GL26 Tumors in Mice. The inventors' model proposes that DCs and/or other antigen presenting cells ("APCs") sample, process, present antigen, become activated, and can then stimulate antigen-specific activation and clonal expansion of cytotoxic T cells. However, it is unclear as to whether DCs migrate to the tumor and process antigen or whether they are presented tumor antigen at the local lymph nodes. While not wishing to be bound by any particular theory, the inventors believe that there should be an accumulation of DCs in the tumor environment. The inventors show herein that CD11c+ cells that are most likely DCs markedly increase in numbers in the immediate vicinity of implanted GL26 tumors implanted in the brains of wild-type immunocompetent C57B/6J mice (FIG. 5). Transgenic CD11cDTR-GFP mice were utilized and carry a transgene encoding a primate diphtheria toxin receptor (DTR)-green fluorescent protein (GFP) fusion protein under control of the murine CD11c promoter that is expressed by DCs (Jung et al., 2002). FIG. 5 shows markedly increased GFP+ cells in the region of the tumor. Immunohistochemical staining using antibodies against GFAP (specific for astrocytes) demonstrated that the tumor was also infiltrated by astrocytes (FIG. 5). No such accumulation of GFP+ DCs or astrocytes occurred on the contralateral non-implanted striatum (FIG. 5B). These results lend further support to the showing that DC migration and/or accumulation in the vicinity of the in vivo implanted GL26 tumor model for GBM. These data provide direct support for the inventors' general model, and also provide indirect support for the DC vaccination therapy described herein.

Furthermore, the inventors have begun to determine the activation state of these GFP positive dendritic cells by immunohistochemistry. These GFP positive dendritic cells were also MHC II positive. The presence and activation of endogenous microglia were also examined by performing IHC against F4/80 for microglia and MHCII in these GL26 implanted mice. F4/80 immunopositive cells were also positive for MHC II in and around the tumor. Furthermore, IHC showed that astrocyte GFAP antigenicity was increased, which suggested an astrogliosis response in the inventors' tumor model. The presence of CD8+ T-cells in and around the tumor was determined by IHC as the inventors believe that these cells play a significant anti-tumor effector role in the vaccination therapy described herein. Indeed CD8+ T-cells were present within the tumor and the inventors plan to further analyze the activated state of these cells under different vaccination paradigms.

Example 5

TLR Activation in the DC 2.4 Mouse Dendritic Cell Line Improves the Efficacy of the Inventors' DC Vaccination Against Glioma The murine DC2.4 glioma cell line was derived from C57BL/6 mice, and is a well-characterized cell line for modeling dendritic cell (DC) vaccination therapy in the inventors' experimental induced glioma model in syngeneic mice.

Figure 12:
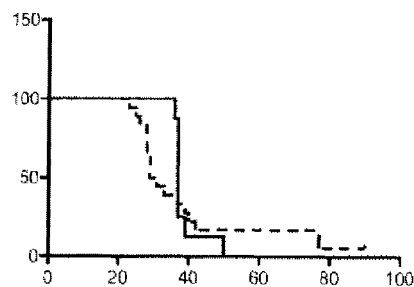
FIG. 12 depicts a TLR Survival Study: Kaplan Meier Curves in accordance with an embodiment of the present invention. GL26 tumorigenic mice received PBMDC vaccination with various TLR adjuvants. A. No vaccination (solid lines) vs. Brain lysate vaccination (dotted lines); B. No vaccination (solid lines) vs. tumor lysate vaccine (dotted lines); C. Tumor lysate vaccine (solid lines) vs. lysate plus Pam3cys vaccine (TLR 2 ligand) (dotted lines); D. Tumor lysate vaccine (solid lines) vs. lysate plus LPS (TLR 4 ligand) (dotted lines); E. Tumor lysate vaccine (solid lines) vs. lysate plus CpG (TLR 9 ligand) (dotted lines); F. Tumor lysate vaccine (solid lines) vs. lysate plus TLR cocktail (TLR 2, 4 and 9 ligands) (dotted lines). *significance.
Figure 12:
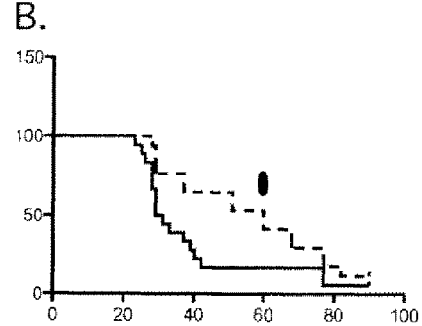
Figure 12:
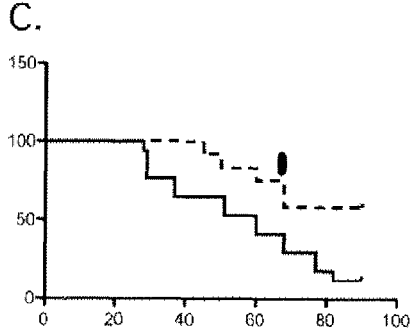
Figure 12:
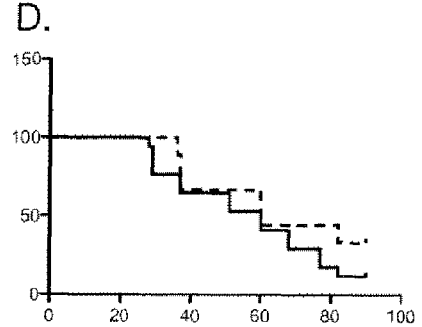
Figure 12:
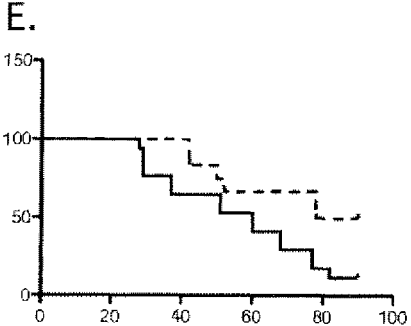
Figure 12:
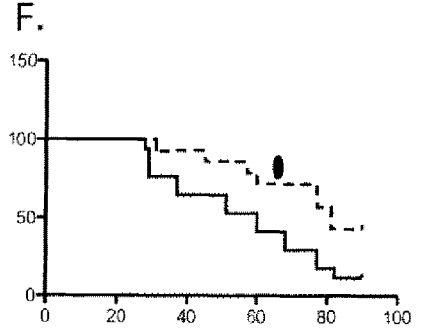

The inventors believe that activation of TLRs acts as an adjuvant to the tumor lysate activated dendritic cell based vaccination. This dendritic cell line is chosen because this cell line has been used for all the inventors' previous vaccination studies and the inventors' vaccination protocol. Furthermore, the inventors propose that primary dendritic cells obtained from multiple animals for these experiments may bring variability in their activation and functional state between animals and potentially introduce variability in immune recognition molecules, including MHCl. The inventors' DC vaccination protocol against Gliomas is a non-tumor antigen specific approach that utilizes GL26 lysate obtained from multiple freeze-thaw cycles. Evidence is provided that adoptive transfer of tumor lysate and TLR cocktail (Pam3cys/TLR2, LPS/TLR4 and CpG/TLR9) activated DC2.4 cells into the experimentally-induced syngeneic GL26 glioma and vaccination mouse model, as described above, significantly improves survival as compared to untreated and GL26 lysate treated DC2.4 vaccination. See e.g., FIG. 12.

Example 6

Exposure of DC2.4 Cells to TLR Ligands Promotes the Gene and Protein Expression of TLR Downstream Targets DC2.4 cells were activated with a cocktail of TLR2, TLR4 and TLR9 specific ligands based on evidence that has examined the potential of individual activated TLRs, including TLR2, TLR3, TLR4, TLR5, TLR7, TLR9 (Pam3cys4, PolyI:C, LPS, ST-FLA, Gardiquimod and CpG ODN, respectively) to promote DC2.4 activation in vitro as measured by increased expression of CD80, CD86 co-stimulatory molecules and pro-inflammatory cytokines, IL6, TNFα, IL-12 and Cox-2. All TLR ligands were used at concentrations proven to be efficacious (data not shown). Exposure of the DC2.4 dendritic cell line to TLR ligands leads to increased expression of CD80 and CD86 protein. The inventors believe that adjuvant therapy with TLR ligands activates DCs, which in turn would involve upregulation of costimulatory molecules. If no upregulation of costimulatory molecules occurred, then DCs would not be capable of adequately activating antigen-specific T cells. The inventors believe that such T cell activation is important both for anti-tumor cytotoxic attack by antigen specific T cells, and also for efficacy of vaccination therapy. Hence, it is important to show that stimulation of DCs in vitro does in fact lead to upregulation of costimulatory molecules.

Figure 6:
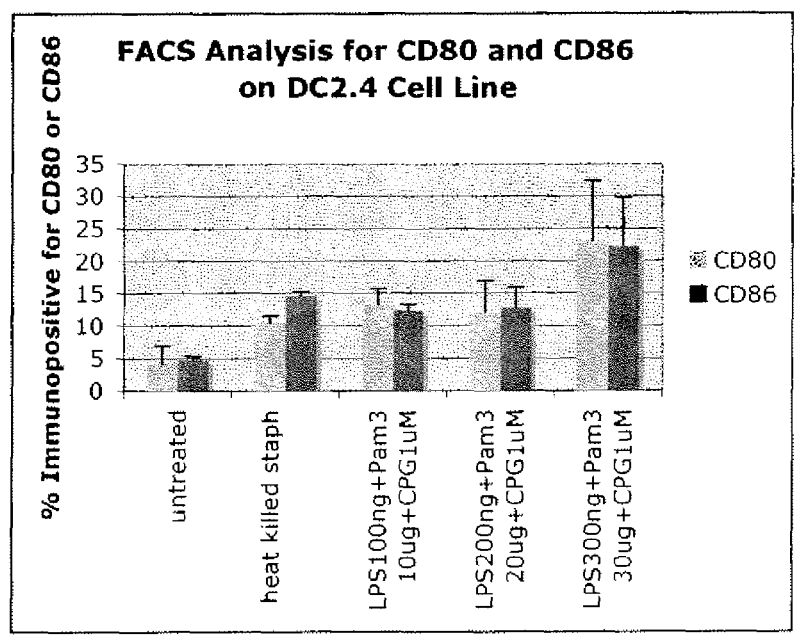
FIG. 6 depicts CD80 and CD86 FACS analysis of untreated DC2.4 cell line versus TLR ligand cocktail-exposed DC2.4 cells, which shows a significant (p<0.001) increase in CD80 and CD88 protein expression in accordance with an embodiment of the present invention.

The inventors show that exposure of the dendritic cell line DC2.4 to TLR ligands in vitro promotes increased expression of co-stimulatory molecules that aid in the activation of T cells. DC2.4 cells are exposed to heat killed *staphylococcus aureus* (Invitrogen, USA) or a cocktail consisting of LPS, Pam3Cys4 and CpG at varying concentrations (FIG. 6). Control DC2.4 cells were cultured identically, but untreated. Immunocytochemistry against CD80 and CD86 and FACS analysis were performed to determine the percent of DC2.4 immunopositive for CD80 and CD86. Treatment with TLR ligand cocktail led to significantly increased expression of both CD80 and CD86 compared to untreated control cells (FIG. 6) (CD80: TLR ligand cocktail treated 13.2+/−2.5 SEM vs. untreated, 4.2+/−2.7 SEM vs.; P<0.001; CD86: TLR ligand cocktail treated, 12.3+/−1.1 SEM vs. untreated, 4.8+/−0.5 SEM; P<0.001). The TLR ligand cocktail consisted of LPS 100 ng+Pam3Cys4 10 µg+CPG 1 µM).

Example 7

TLR Receptor Activation is MyD88 Dependent and TRIF Dependent

Figure 7:
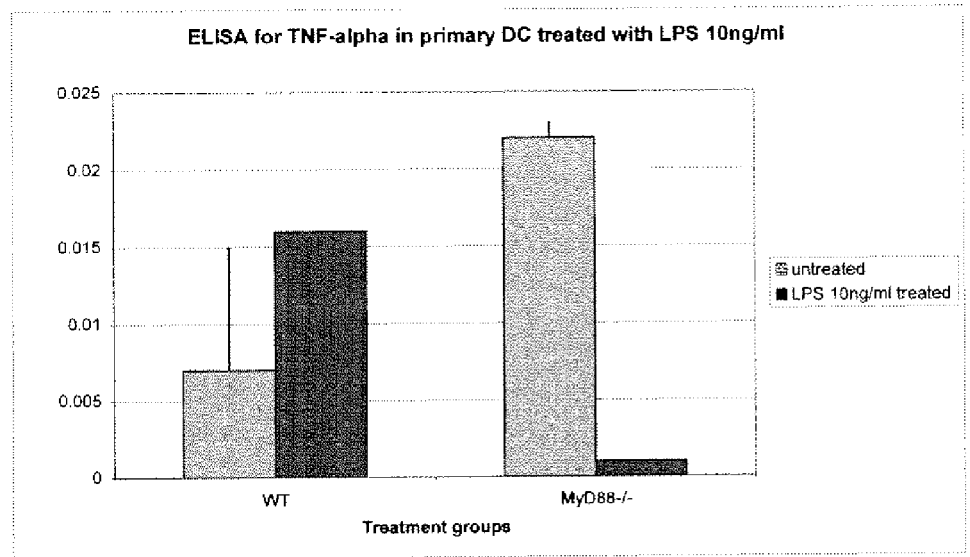
FIG. 7 depicts ELISA for TNF-alpha in primary DC treated with LPS in accordance with an embodiment of the present invention.

While the inventors provide evidence that GL26 tumor cells and TLR ligands activate DC2.4 cells, it is unknown if GL26 lysate activation is signaling through MyD88−/− and/ or TRIF dependent pathways. It is possible that the GL26 tumor cell activation is signaling through TLRs or at least through downstream signaling molecules MyD88 and/or TRIF. Therefore, the inventors isolated primary dendritic cells from MyD88−/− and wild-type controls and exposed them to GL26 lysate and TLR ligand LPS. The inventors believe that LPS activation in MyD88−/− DC will not show up-regulation of TNF-alpha protein as measured by ELISA. The inventors show herein evidence that LPS does signal through the MyD88 pathway, as MyD88−/− DC exposed to LPS showed no up-regulation of TNF-alpha protein as measured by ELISA, while wild-type DCs show significant up-regulations of TNF-alpha protein compared to controls (FIG. 7).

Example 8

DC Vaccination Promotes Splenocytes IFNγ Response, CTL Activity, and Increases the Number of Activated DC 2.4 Cells, CD4+ and CD8+ T-Cells DC based vaccination relies on the fact that activated DC subsequently activate T-cells, some of which are effector anti-tumor CD8+ T cells. A common assay used to determine the anti-tumor cytoxic T cell effect is to isolate splenocytes from tumor bearing mice and co-culture these cells with tumor cells to subsequently measure tumor cell viability. Therefore, isolated splenocytes have been isolated from GL26 tumor bearing mice that underwent GL26 lysate DC vaccination with or without TLR cocktail adjuvants ex vivo. Subsequently, these cells were co-cultured with GL26 tumor cells and various ratios (e.g., 50:1, 25:1, 12.5:1, splenocytes (effectors): GL26 (targets)) determine cell viability. A trend of increasing GL26 cell death is shown when comparing mice vaccinated with GL26 and TLR ligand treated DC versus GL26 treated DC alone.

Example 9

DC Treatment with TLR Ligands Enhance the Efficacy of Ex Vivo DC Vaccination in Preclinical Model The inventors believe that ex vivo dendritic cell activation with TLR2, TLR4 and TLR9 ligands produce an adjuvant effect that enhances the efficacy of glioma vaccination therapy. Survival of tumor-implanted mice was significantly improved after ex viva treatment of bone marrow-derived DCs (BMDCs) with TLR ligands and tumor lysate as compared to tumor lysate alone. BMDCs were treated ex vivo with GL26 tumor lysate and with ligands for TLR2, TLR4, and TLR9, (Pam3Cys, LPS and CpG ODN, respectively) and compared to DC activation against GL26 lysate activation or normal brain lysate activation by measuring protein expression levels of TLR downstream targets (TNF-α, IL-6, IL-12), CD40 and CD86 costimulatory molecules. CD80 may also be measured. The efficacy of TLR adjuvants and tumor lysate BMDC vaccination in vivo against GL26 glioma compared to tumor lysate BMDC activation alone was also determined.

Exposure of primary bone marrow derived dendritic cells (BMDC) to TLR ligands in vitro differentially promotes increased expression of DC activation marker CD40, CD86 co-stimulatory molecules and the production of IL6, TNF-α and IL-12 cytokines. (See FIG. 8.)

Figure 8:
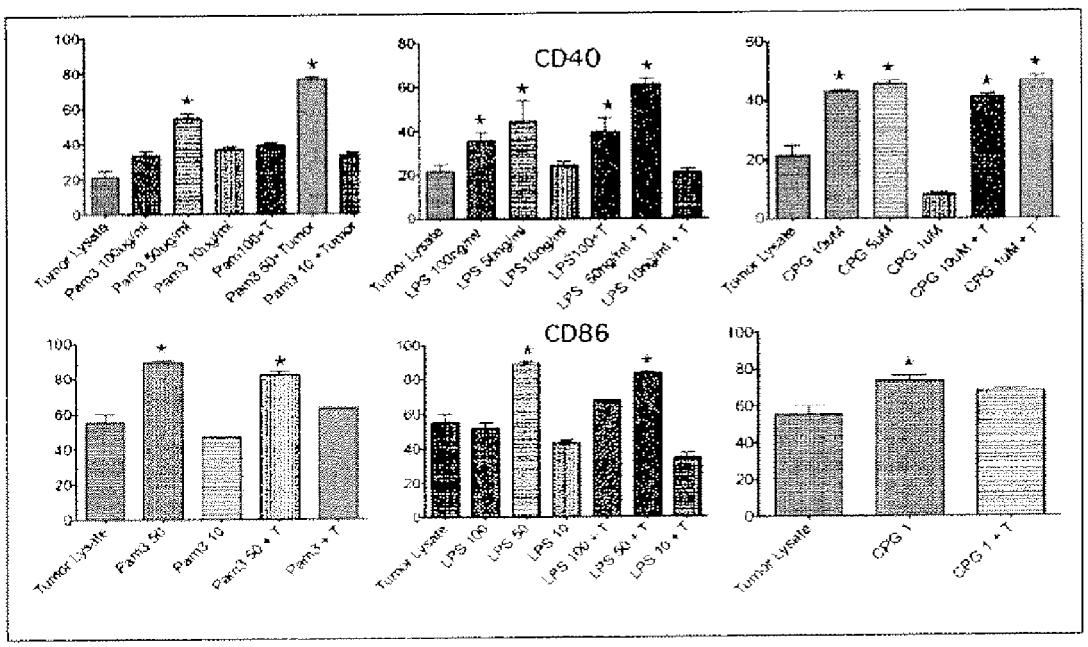
FIG. 8 depicts FACS against BMDC: GL26 Tumor Lysate vs. TLR ligands in accordance with an embodiment of the present invention. CD40 and CD86 panels show an increase in the % CD40 and CD86 immunopositive BMDC after treatment with GL26 Lysate plus TLR adjuvants at specific concentrations (ug/ml) (One way ANOVA, *=P<0.05). Error bars represent SEM.
Figure 9:
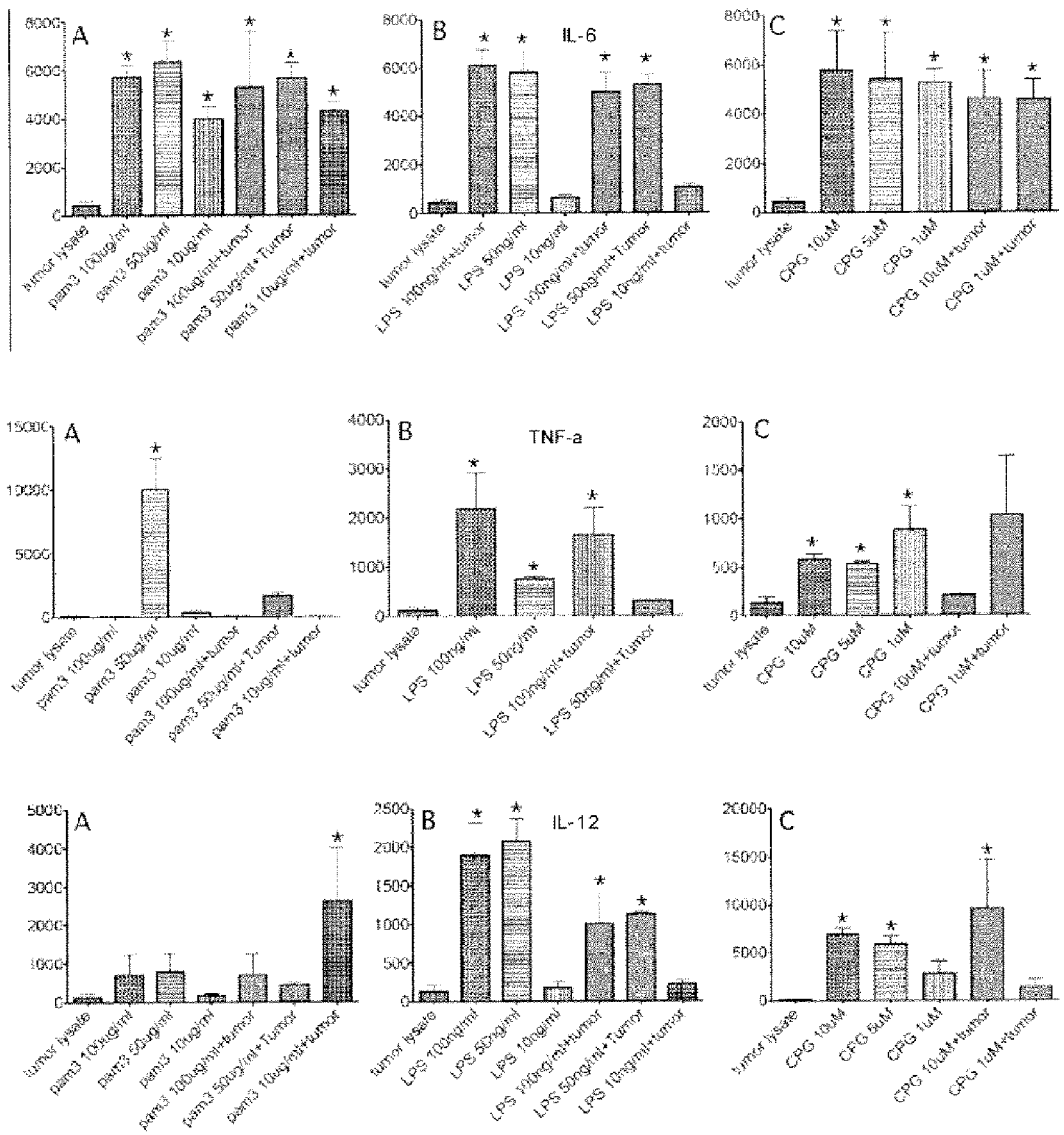
FIG. 9 depicts IL-6, TNF-$\alpha$ and IL-12 ELISA of BMDC activated by GL26 lysate vs. TLR ligands in accordance with an embodiment of the present invention. Top panel shows that IL-6 secreted protein from BMDC activated by GL26 lysate plus TLR ligands for all TLR ligands is significantly increased. Middle panel shows TNF-$\alpha$ secreted protein and differential increases based on TLR concentrations. Bottom panel shows IL-12 secreted protein and differential increases. Error bars represent SEM. Pam3cys/TLR2 overall shows relatively limited increases in IL-12 protein production (pg/ml). (ANOVA, *=P<0.01). Error bars represent SEM.

Experiments were performed with at least three replicates per condition. As controls for these experiments the inventors utilized brain tissue lysate obtained from healthy C57BL/6 mice and untreated DCs. Furthermore, for each TLR ligand, the inventors utilized up to three different concentrations previously shown to activate dendritic cells in order to identify the best concentration for maximal activation of BMDC. Flow cytometric analysis data suggests that GL26 tumor lysate and individual TLR adjuvants differentially activate BMDC to a significantly greater degree than GL26 tumor lysate alone based on CD40 and CD86 expression (FIG. 8). The inventors have also examined the expression of CD86 and MHCII and data suggests a trend in the increase of expression but no significant difference between GL26 lysate and lysate plus TLR adjuvants from one independent experiment (data not shown). However, TLR ligands alone consistently promote increases the dependent variables measured to a greater degree than TLR ligands with tumor lysate. However, it is likely that activation by TLR ligands alone would not prime T cells to be tumor antigen specific. Hence, the combination of TLR adjuvants and GL26 lysate are utilized for survival studies. Furthermore, the inventors sought to determine if DC vaccination with TLR adjuvants increased the production of secreted cytokines suggests to promote T cell activation, reviewed by Wang et al. (*Toll-like receptors and immune regulation: implications for cancer therapy*. ONCOGENE 27:181-189). Therefore, ELISA on BMDC treated with GL26 lysate and individual TLR ligands were performed as described above. Data overall suggests that TLR adjuvants differentially but significantly increase the production of pro-inflammatory and T cell priming cytokines, including IL-6, TNF-α and IL-12 (FIG. 9).

Example 10

Determination and Comparison of the Effectiveness of Treatment of BMDCs ex vivo with Individual TLR Ligands on Tumor Cell Lysate Activation of Dendritic Cells The inventors believe that adjuvant treatment of BMDCs ex vivo with TLR2, 4 and 9 ligands further activates dendritic cells compared to tumor cell lysate activation alone. The inventors believe that activation of TLR ligands in primary BMDCs shows a significant increase in expression of the dependent variables, CD40, TNF-α, IL-6 and IL-12, and co-stimulatory molecules CD80 and CD86 over that of GL26 lysate activation alone. All of these molecules have been shown to generate a pro-inflammatory Th1 response and stimulate T-cells against tumors.

Example 11

TNF-α, IL-6, IL-12, CD80, CD86 and CD40 Expression Analysis

Primary BMDC cell culture and TLR ligand exposure: Primary BMDCs were isolated from the femurs of 6-10 week old C57BL/6 mice and cultured in RPMI cell culture media with GM-CSF (1000 IU/ML) and IL-4 (1000 IU/ML). BMDCs ($1 \times 10^6$ cells/ml) were maintained in cell culture at 37° C., 5% $CO_2$ and exposed to with 150 mg GL26 freeze-thaw lysate and either TLR2 ligand (Pam3Cys, 50 μg/ml), TLR4 ligand (LPS 50 ng/ml), or TLR9 ligand (CpG ODN 1826, 5 μM) overnight (ON). Control cells were treated with 150 mg GL26 freeze-thaw lysate only. To control for the possibility that effects on DCs are due to nonspecific stimulation with brain tissue and are unrelated to the tumor per se, a separate set of experiments treats DCs with lysate isolated from normal age-matched mouse forebrain and/or striatum, the location at which the tumor was implanted. These TLR ligand concentrations are based the inventors' evidence after testing LPS at 100 ng/ml, 50 ng/ml and 10 ng/ml; Pam3Cys at 100 µg/ml, 50 µg/ml and 10 µg/ml, CpG ODN at 10 µM, 5 µM and 1 µM. ELISA data demonstrated that the concentrations selected either induced maximum secretion of dependent variable proteins, or there was no dose-response effect, in which case the inventors chose the lowest concentrations for the analysis. To verify that effects of stimulation by cells with TLR ligand were indeed due to TLR-dependent signaling and to exclude nonspecific effects, experiments are repeated using BMDCs isolated from the appropriate knockout mice (i.e., Pam3Cys stimulation with TLR2−/− and TLR2+/+ BMDC, LPS stimulation with TLR4−/− and TLR4+/+ BMDC, and CpG ODN stimulation with TLR9+/+ and TLR9−/− BMDC.

Flow Cytometry: For cell surface protein expression of CD86 and CD40, FACS analysis was performed. Cultured BMDCs are immunostained with the following antibodies: CD40-PE and CD86-PE. All antibodies were incubated with culture cells for 30 minutes in 5% normal goat serum in FACS buffer (0.1 MPB with 0.01% Triton-X 100) on ice and washed for flow cytometric analysis. For non-fluorophore conjugated primary antibodies, cells were incubated with appropriate secondary Ab at a concentration of 1:250 in FACS buffer for 30 minutes on ice. Dual fluorescent signals on cells were analyzed by FacScan II cytometer with equivalent gain, and gates for positive staining set according to negative (appropriate IgG secondary antibodies only) controls, and analysis performed with CellQuest software. Percentage of immunopositive cells and mean fluorescent intensity were determined, averaged and compared between groups by T-test or ANOVA and appropriate post-hoc test. Three independent experiments with at least three replicates per experiment were performed to ensure reproducibility and allow statistical comparisons.

For cell surface protein expression of CD11c, CD80, FACS analysis can also be performed as described above using anti-CD11c-FITC or anti-CD11c-PE to identify BMDCs.

ELISA: Briefly, BMDCs were cultured in 24-well plates at $3 \times 10^5$ cells/ml and exposed to TLR ligands and lysate for 24 hours. Cell culture media were collected for ELISA analysis against IL-6, TNF-α and IL-12. Three independent experiments with at least three replicates per experiment were performed.

Example 12

Determination of the Effectiveness of Individual TLR Ligands Combined with Tumor Cell Lysate vs. Tumor Lysate Alone in DC-Based Vaccination (ex vivo Treatment of BMDCs with Tumor Lysate Followed by Adoptive Transfer into Mice) Against Glioma The inventors believe that glioma bearing mice vaccinated with tumor lysate and TLR ligand activated BMDCs show significantly slower tumor growth, and survive longer than mice vaccinated with BMDCs activated by tumor cell lysate alone.

Intracranial GL26-GFP glioma implantation: GL26 cells that express a transgene for GFP were implanted in mice.

Dendritic cell vaccination: Primary BMDC were isolated from wild-type, TLR2−/−, TLR4−/−, and TLR9−/− mice (and their wild-type littermate controls) and treated as described above. $5 \times 10^4$ GL26 lysate-pulsed BMDCs are injected s.c. on days 3 and 7 post-tumor implantation. Two mice of each genotype yielded enough BMDCs for DC vaccination in each experimental group. TLR2−/− and TLR2+/+ mice were exposed to Pam3Cys, TLR4−/− and TLR4+/+ mice are exposed to LPS, and TLR9−/− and TLR9+/+ mice are exposed to CpG ODN ON.

Euthanasia: Separate cohorts of mice were euthanized at 14 and 21 days after tumor implantation (to assess pre-terminal effects), and upon acquisition of terminal neurological symptoms (to assess terminal effects), and their brains removed for analysis of tumor volume and invasiveness. Separate cohorts of mice were euthanized for primary DC isolation. Acquisition of neurological symptoms were assessed by Veterinary Medicine staff, who determines (in blinded fashion) when sacrifice of mice is necessary.

In vivo analysis of Tumor Size/Volume-microCT Imaging: Based on previous experience, on average wild-type C57BL/6 mice survive approximately 30 days after tumor implantation. The presence or absence of tumor and the tumor volume was determined by micro CT at day 14 and 21 after tumor. Furthermore, animals euthanized at day 14 and 21 have their brains removed and fixed and undergo microCT scanning and analysis. A quantitative morphometric analysis of the tumor volume was assessed with the aid of microCT scanning (microCT 40; Scanco, USA). For each animal, the area of tumor formation in the injection site was scanned, marked, and measured using CT 3D reconstruction and an analysis of total tumor volume ($mm^3$). Relative values between groups were averaged and compared.

Alternate In vivo analysis of tumor size—H&E: Upon euthanasia, mice were perfused with 4% paraformaldehyde in phosphate buffer and their brains removed. Brains are frozen from cohorts of these mice and 10 mm tumor tissue sections stained with H&E. Numbers of non-contiguous tumors containing at least 5 cells within 4-8 tissue sections surrounding the caudate putamen were counted under 10× magnification. Non-contiguous tumors were quantified within selected regions throughout the brain, and plotted as the percentage of at least 5 mice with ≥1 tumor within each structure.

Survival monitoring: Mice were immediately euthanized upon acquisition of terminal neurological symptoms. Time from tumor implantation to euthanasia indicates survival time/death event. Survival times from individual mice in the same experimental group were compared against those of control groups by Kaplan-Meier analysis using log-rank to assess significant differences. Euthanization of all animals are performed according to the IACUC Animal Safety Standards. The survival study ends at 90 days post-implantation. All surviving mice were euthanized at 90 days and considered by Kaplan-Meier analysis. However, euthanization at 90 days is not considered a death event.

The inventors believe that repeated flow cytometric analyses and ELISA analyses of the above stated proteins demonstrate that activation of TLR2, TLR4 and TLR9 in primary BMDCs significantly increases the expression of the dependent variables over that of GL26 lysate activation alone. The inventors believe that there are differential survival between groups: non-vaccinated animals have the shortest survival times, followed by animals vaccinated with GL26 tumor lysate activated BMDC. As MyD88 signaling is required for all TLRs examined, it may be difficult to predict which TLR treated group will survive longer. Nonetheless, since TLR4 signals through both MyD88 and TRIF, it is possible that this group may show differential survival compared to TLR2 and TLR9 stimulated groups. The inventors do not believe that there is a difference in survival of mice vaccinated with primary BMDCs isolated from TLR knockout mice compared to wild-type littermate controls. Furthermore, these data begin to elucidate if tumor lysate signals through TLR 2, 4 or 9.

Example 13

Tumor Lysate and Adjuvant Treatment with TLR Ligands is Solely MyD88 Dependent While not wishing to be bound by any particular theory, the inventors believe that ex vivo treatment of primary BMDCs with TLR ligands exerts an adjuvant effect that requires intact MyD88-dependent signaling. The inventors believe that survival of tumor implanted mice vaccinated with BMDCs obtained from MyD88−/− and treated ex vivo with tumor lysate and TLR ligands (e.g., Pam3Cys/TLR2 is MyD88 dependent, LPS/TLR4 is MyD88/TRIF dependent and CpG ODN/TLR9 is MyD88 dependent) does not significantly increase expression of the dependent variables or improve survival, as compared to mice vaccinated with BMDCs obtained from MyD88+/+ littermate controls. Hence, in the absence of MyD88-dependent signaling, adjuvant effect is partially or completely abolished. It is also determined if tumor cell lysate promotes up-regulation of the dependent variables through MyD88 signaling. As tumor lysate has been used to activate BMDCs for vaccination therapy against glioma, as well as, tumor specific antigens, it is possible that tumor lysate may contain proteins that activate MyD88 signaling or even activate TLRs. In order to begin to elucidate the mechanism by which tumor lysate activates dendritic cells, the dependent variables after tumor lysate activation in primary BMDCs obtained from MyD88−/− mice and their wild-type littermates as controls were measured. Furthermore, in order to determine if any effect demonstrated through GL26 lysate activation of BMDCs is specific to tumor cells or is represented by non-cell type specific lysis, normal brain cells were used as controls.

The inventors believe that mice vaccinated with GL26 lysate activated primary DCs and GL26 lysate and TLR ligand activated primary DCs from MyD88−/− will not survive longer than controls vaccinated with primary DCs obtained from wild-type littermate controls. As the TLR ligands all signal through MyD88 intracellular signaling, in the absence of this molecule, it is expected that no benefit from the addition of the proposed TLR ligands is seen, except possibly for LPS. LPS partially signals through TRIF independently of MyD88, hence there may be some improvement in the efficacy of DC based vaccination against glioma.

Figure 10:
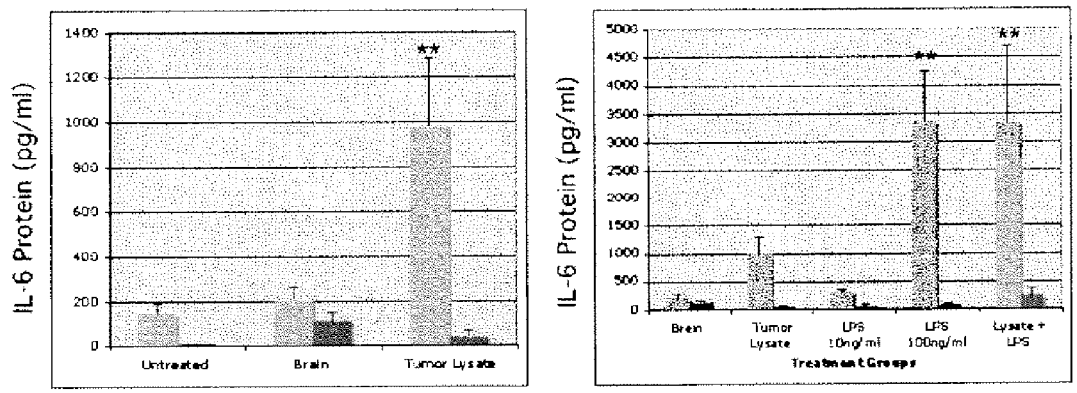
FIG. 10 depicts IL-6 ELISA from primary BMDC derived from MyD88−/− and littermate controls in accordance with an embodiment of the present invention. Top panel shows wild-type BMDC in light grey and MyD88−/− in dark grey. BMDC exposed to tumor lysate and TLR adjuvants show significant increase IL-6 production compared to brain. (ANOVA, *=P<0.01).
Figure 11:
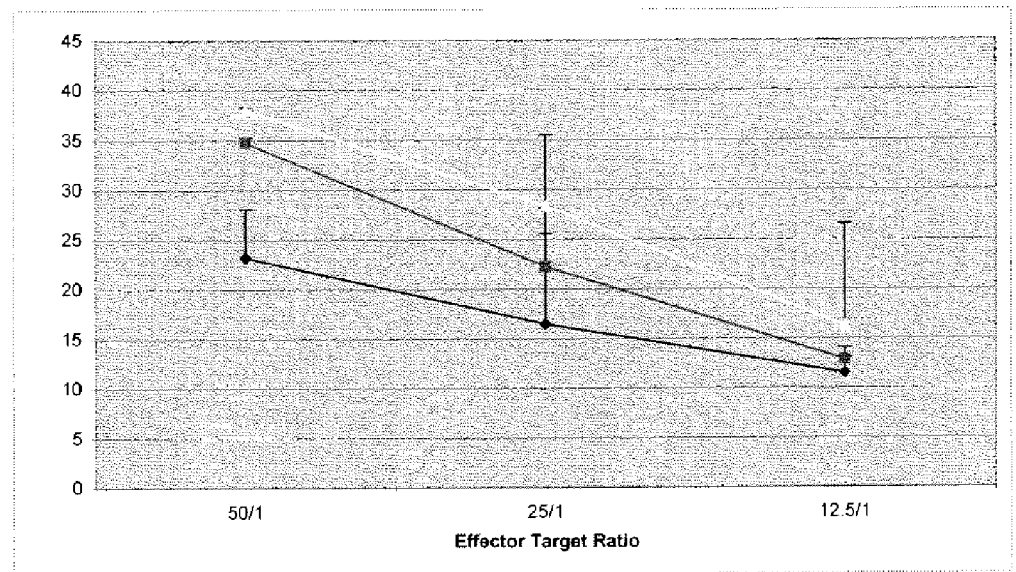
FIG. 11 depicts splenocytes isolated from GL26 tumor bearing mice (triangle), GL26 DC vaccinated mice (square) and GL26 with TLR cocktail adjuvant DC vaccination (diamond) in accordance with an embodiment of the present invention.

While the inventors provide evidence that GL26 tumor cells and TLR ligands activate primary BMDC. The inventors did not know if GL26 lysate activation is signaling through MyD88−/− dependent pathways. It is possible that the GL26 tumor cell activation is signaling through TLRs or at least through downstream signaling molecule MyD88. Therefore, primary dendritic cells from MyD88−/− and Wild-type controls were isolated and exposed to GL26 lysate and TLR ligand LPS at 100 ng/ml or 10 ng/ml. The inventors believe that LPS activation in MyD88−/− DC will not show up-regulation of secreted IL-6 protein as measured by ELISA. Shown herein is evidence that suggest LPS does signal through the MyD88 pathway as MyD88−/− DC exposed to LPS showed reduced IL-6 secreted protein levels compared to BMDC derived from wild-type littermate controls as measured by ELISA. Furthermore, no significant difference exists between MyD88−/− and wild-type derived BMDC exposed to brain lysate (FIG. 10). These data support of the claim that TLR receptor activation with tumor lysate is part of the MyD88 dependent pathway.

Primary BMDCs Isolation: Primary BMDCs were isolated from the bone marrow of femurs of euthanized MyD88−/− and their +/+ littermate controls as described above. BMDCs were activated using 1) GL26 tumor lysate alone; 2) TLR ligands (Pam3cys (50 µg/ml) or LPS (50 ng/ml) or CpG CDN (5 µM) and tumor lysate for each; 3) Treatment of DCs with brain lysate alone may also serves as a control condition.

GL26 tumor implantation and subsequent DC vaccination were as described above.

Euthanasia: Separate cohorts of mice were euthanized 14 days after tumor implantation (to assess pre-terminal affects) and upon acquisition of terminal neurological symptoms (to assess terminal affects), and their brains removed for analysis of tumor invasiveness. Separate cohorts of mice were euthanized for primary DC isolation.

Tumor volume and survival were measured as described above.

Example 14

TLR Adjuvants Promote Effector CD8+ T-Cell Activation After TLR Adjuvant Vaccination Therapy in Preclinical Model While not wishing to be bound by any particular theory, the inventors believe that the enhanced activation of dendritic cells through TLR ligation improves the efficacy (e.g., increase survival and smaller relative tumor volume) of DC based vaccination therapy against glioma by promoting the anti-tumor effects of cytotoxic CD8+ T-cells. It was determined if there is an increase in the absolute number of activated DCs (e.g., CD11c+ and CD80+, CD86+ and CD40+), TCRα+/CD4+ T-cells and TCRα+/CD8+ T-cells in the cervical lymph nodes and spleen, as well as, the cytotoxic T-lymphocyte (CTL) activity and IFN-γ expression levels of splenic tumor specific, TRP-2+/CD8+ T-cells in mice that underwent GL26 lysate DC vaccination with or without TLR ligands. Furthermore, it is determined if vaccination against GL26 tumor is effective in CD8−/− or CD4−/− mice.

Example 15

Determination and Comparison of the Number of Activated DCs (CD11C+, CD80+, CD86+ and CD40+) in Cervical Lymph Nodes and Spleen The inventors believe that tumor lysate with TLR adjuvant DC vaccination promotes the accumulation of activated DCs in cervical lymph nodes to a greater degree than tumor lysate DC vaccination alone and thus, be an increase in the absolute number of activated DCs in mice vaccinated with tumor lysate and TLR ligand activated DCs as compared to DCs activated with tumor lysate alone.

BMDC isolation, GL26 tumor implantation and subsequent DC vaccination are as described above. Four experimental groups are euthanized for immune cells analyses 1) GL26 implant with no vaccination 2) GL26 implant with tumor lysate activated DC vaccination 3) GL26 implant with tumor lysate activated DC vaccination and TLR adjuvants.

Cervical lymph nodes and spleens are isolated 14 days after tumor implantation. Animals are euthanized; lymph nodes and spleens are surgically removed and dissociated in a PBS-based buffer. Mononuclear cells are purified by Ficoll gradient and PBMC are concomitantly stained with anti-CD11c/anti-CD80, anti-CD11c/anti-CD86, and anti-CD11c/ anti-CD40, followed by flow cytometric analysis. Specific expansion of activated DCs, is calculated as the percentage of CD11c+/CD40+ cells from tumor-bearing wild-type or vaccinated wild-type mice, divided by the percentage of such cells in naïve (non-tumor-bearing) mice. The percentage increase of each cell type is determined for each group and compared.

Euthanasia: Separate cohorts of mice are euthanized at 14 days after tumor implantation. Separate cohorts of mice are euthanized for primary DC isolation.

Example 16

Determination of the IFN-γ Expression Levels and Cytolytic TRP-2$^+$/CD8$^+$ T-Cells After Challenge with Tumor Lysate in Mice that Received Anti-GEM DC Vaccination with or Without TLR Adjuvant Treatment of DCs Prior to Adoptive Transfer The inventors believe that TRP-2$^+$/CD8$^+$ T cells obtained from glioma-implanted mice that received BMDC treated with both tumor lysate and TLR adjuvants express greater amounts of IFN-γ compared to splenocyte-derived TRP-2$^+$/CD8$^+$ T cells obtained from mice receiving BMDC treated with tumor lysate alone. Based on their data, the inventors believe that splenic TRP-2$^+$/CD8$^+$ T-cells obtained from experimentally-induced GL26 glioma vaccinated with BMDC activated by tumor lysate and TLR ligands have a significantly greater cytolytic response and increased expression of IFN-γ as compared to BMDC activated by tumor lysate alone.

Based on preliminary evidence, the inventors believe that the absolute number of TRP-2+/CD8+/IFNγ+ splenocytes are significantly greater from mice vaccinated with tumor lysate and TLR adjuvant activated BMDC as compared to those vaccinated with tumor lysate activated BMDC or non-vaccinated GL26 tumor bearing mice. Furthermore, the inventors believe that TRP-2+/CD8+/IFNγ+ splenocytes derived from tumor lysate and TLR adjuvant DC vaccinated mice produces significantly greater amounts of secreted IFNγ protein compared to the other experimental groups.

BMDC isolation, GL26 tumor implantation and DC vaccination are performed as described above.

IFN-γ flow cytometric analysis and ELISA: Splenocytes are isolated as described above and immunostained against TRP-2$^+$/CD8$^+$ T-cells and anti-IFN-γ with Golgi stop, and undergo flow cytometric analysis. Splenocytes derived from different treatment groups are compared. For ELISA, splenocytes undergo FACS against TRP-2+/CD8+ T-cells and are plated in 24-well plates at 2×10$^5$/ml for up to 3 days in RPMI and IL-2 (20 IU/ml) and re-stimulated with GL26 tumor cell lysate. Secreted IFN-γ protein is measured by the IFN-γ ELISA kit.

Euthanasia: Separate cohorts of mice are euthanized at 14 days after tumor implantation. Separate cohorts of mice are euthanized for primary DC isolation.

Example 17

Determination of the Cytolytic Activity of CD8+ T Cells Derived from Glioma-Implanted Mice Receiving TLR Adjuvants with DC Vaccination Compared to Mice Receiving BMDC Treated with Tumor Lysate Alone The inventors believe that splenocyte-derived CD8+ T cell cytolytic activity is further enhanced in glioma bearing mice vaccinated with BMDC activated by tumor lysate and TLRs as compared to tumor lysate alone. As such, it is believed that the T cell cytotoxic effect on GL26 tumor cells are significantly increased in CD8+ splenocytes derived from tumor lysate and TLR adjuvant DC vaccinated mice compared to tumor lysate activated DC vaccinated mice and non-vaccinated controls.

CTL assay TCR Splenocytes were FACS sorted against TCRα+/CD8+ (effectors) and re-plated in culture with IL-2 (20 IU/ml) and GL26 tumor lysate for up to 3 days and then co-cultured with GL26 cells (Target) in growth phase at E:T ratios of 50:1, 25:1 and 12.5:1, Cultures were then analyzed using the CTL-LDH kit (Roche Diagnostics, Mannheim, Germany) to determine cytotoxicity.

DC vaccination promoted splenocyte derived cytotoxic T lymphocyte activity. DC based vaccination relies on the fact that activated DC subsequently activate T cells, some of which are effector anti-tumor CD8+ T cells. A common assay used to determine the anti-tumor cytotoxic T cell (CTL) effect is to isolate splenocytes from tumor bearing mice and co-culture these cells with tumor cells to subsequently measure tumor cell viability. Therefore, the inventors have isolated splenocytes from GL26 tumor bearing mice that underwent either GL26 lysate DC vaccination with or without TLR cocktail adjuvants as described above and were subsequently euthanized 2 weeks after tumor implantation. Splenocytes were isolated and co-cultured with GL26 tumor cells and various ratios (e.g., 50:1, 25:1, 12.5:1, splenocytes (effectors): GL26 (targets) cells ratios for up to three days and determine cell viability through the use of the LDH-CTL assay (Roche), as described above. Data shows that there is a trend towards increase splenocyte cytotoxicity in mice that were vaccinated with DCs activated with GL26 lysate and TLR adjuvants or vaccinated with DC activated by GL26 lysate alone as compared to mice with no vaccination.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. A composition comprising:
   a dendritic cell pulsed in vitro with brain tumor lysate and at least one toll-like receptor (TLR) ligand, wherein the at least one TLR ligand is a combination of a TLR2 ligand, a TLR4 ligand, and a TLR9 ligand; and
   a pharmaceutically acceptable carrier.

2. The composition of claim 1, wherein the TLR2 ligand is selected from Pam3cys4, HKLM, or FSL1, the TLR4 ligand is lipopolysaccharide (LPS), and the TLR9 ligand is CpG ODN.

3. The composition of claim 2, wherein the at least one TLR ligand is a combination of Pam3cys, LPS and CpG ODN.

4. The composition of claim 1, wherein the brain tumor lysate is selected from the group consisting of glioma, glioblastoma, glioblastoma multiforme (GBM), oligodendroglioma, primitive neuroectodermal tumor, astrocytoma, ependymoma, oligodendroglioma, medulloblastoma, meningioma, pituitary carcinomas, neuroblastoma, and craniopharyngioma.

5. The composition of claim 1, wherein the brain tumor lysate is from a glioma.

6. The composition of claim 1, wherein the TLR2 ligand is Pam3cys4, the TLR4 ligand is lipopolysaccharide (LPS), and the TLR9 ligand is CpG ODN.

7. A method of eliciting a specific immune response in a mammal in need thereof, comprising:
   providing a composition comprising:
      a dendritic cell pulsed in vitro with brain tumor lysate and at least one toll-like receptor (TLR) ligand, wherein the at least one TLR ligand is a combination of a TLR2 ligand, a TLR4 ligand, and a TLR9 ligand, and
      a pharmaceutically acceptable carrier; and
   administering the composition to the mammal to elicit the specific immune response.

8. The method of claim 7, wherein the dendritic cell is an autologous dendritic cell.

9. The method of claim 7, wherein the dendritic cell is an allogeneic dendritic cell.

10. The method of claim 7, wherein the TLR2 ligand is selected from Pam3cys4, HKLM, or FSL1, the TLR4 ligand is lipopolysaccharide (LPS), and the TLR9 ligand is CpG ODN.

11. The method of claim 10, wherein the at least one TLR ligand is a combination of Pam3cys, LPS and CpG ODN.

12. The method of claim 7, wherein the brain tumor lysate is selected from the group consisting of glioma, glioblastoma, glioblastoma multiforme (GBM), oligodendroglioma, primitive neuroectodermal tumor, astrocytoma, ependymoma, oligodendroglioma, medulloblastoma, meningioma, pituitary carcinomas, neuroblastoma, and craniopharyngioma.

13. The method of claim 7, wherein the brain tumor lysate is from a glioma.

14. The method of claim 7, wherein eliciting a specific immune response treats a brain tumor.

15. The method of claim 14, wherein the brain tumor is selected from the group consisting of glioma, glioblastoma, glioblastoma multiforme (GBM), oligodendroglioma, primitive neuroectodermal tumor, astrocytoma, ependymoma, oligodendroglioma, medulloblastoma, meningioma, pituitary carcinomas, neuroblastoma, and craniopharyngioma.

16. The method of claim 14, wherein the brain tumor is a glioma.

17. The method of claim 7, wherein the TLR2 ligand is Pam3cys4, the TLR4 ligand is lipopolysaccharide (LSP), and the TLR9 ligand is CpG ODN.

18. A method of activating dendritic cells, comprising:
   providing at least one toll-like receptor (TLR) ligand; and
   pulsing a dendritic cell with the at least one TLR ligand, wherein at least one TLR ligand is a combination of a TLR2 ligand, a TLR4 ligand, and a TLR9 ligand.

19. The method of claim 18, wherein the TLR2 ligand is selected from Pam3cys4, HKLM, or FSL1, the TLR4 ligand is lipopolysaccharide (LPS), and the TLR9 ligand is CpG ODN.

20. The method of claim 19, wherein the at least one TLR ligand is a combination of Pam3cys, LPS and CpG ODN.

21. The method of claim 18, further comprising pulsing the dendritic cell with a brain tumor lysate.

22. The method of claim 21, wherein the brain tumor lysate is selected from the group consisting of glioma, glioblastoma, glioblastoma multiforme (GBM), oligodendroglioma, primitive neuroectodermal tumor, astrocytoma, ependymoma, oligodendroglioma, medulloblastoma, meningioma, pituitary carcinomas, neuroblastoma, and craniopharyngioma.

23. The method of claim 21, wherein the brain tumor lysate is from a glioma.

24. The method of claim 18, wherein the TLR2 ligand is Pam3cys4, the TLR4 ligand is lipopolysaccharide (LPS), and the TLR9 ligand is CpG ODN.

25. A kit for eliciting a specific immune response in a mammal in need thereof, comprising:
   a composition comprising:
      a dendritic cell pulsed with brain tumor lysate and at least one toll-like receptor (TLR) ligand, wherein the at least one TLR ligand is a combination of a TLR2 ligand, a TLR4 ligand, and a TLR9 ligand, and
      a pharmaceutically acceptable carrier; and
   instructions for administering the composition to the mammal to elicit the specific immune response.

* * * * *